(12) United States Patent
Barbut et al.

(10) Patent No.: US 8,167,923 B2
(45) Date of Patent: May 1, 2012

(54) COOLING OF LOCALIZED AREAS OF THE BODY FOR CEREBRAL BLOOD FLOW AUGMENTATION

(75) Inventors: Denise Barbut, San Diego, CA (US); Wanchung Tang, Rancho Mirage, CA (US)

(73) Assignee: BeneChill Inc., San Diego, CA (US)

( * ) Notice: Subject to any disclaimer, the term of this patent is extended or adjusted under 35 U.S.C. 154(b) by 352 days.

(21) Appl. No.: 12/578,135

(22) Filed: Oct. 13, 2009

(65) Prior Publication Data

US 2010/0100161 A1 Apr. 22, 2010

Related U.S. Application Data

(60) Provisional application No. 61/104,619, filed on Oct. 10, 2008.

(51) Int. Cl.
*A61F 7/12* (2006.01)
(52) U.S. Cl. .................. 607/105; 607/104; 607/113
(58) Field of Classification Search .......... 607/104–106, 607/113
See application file for complete search history.

(56) References Cited

U.S. PATENT DOCUMENTS

| 6,942,686 | B1 | 9/2005 | Barbut et al. | |
| 7,189,253 | B2 * | 3/2007 | Lunderqvist et al. | 607/105 |
| 2008/0004613 | A1 | 1/2008 | Barbut et al. | |
| 2010/0292765 | A1 * | 11/2010 | Etwil | 607/105 |

OTHER PUBLICATIONS

Guan, et al. "Abstract 2412: Rapid Induction of Head Cooling by the Intranasal Route During Cardiopulmonary Resuscitation improves Survival and Neurological Outcomes," *Circulation*, vol. 116 pp. II_529-II_530, 2007.

* cited by examiner

*Primary Examiner* — Roy Gibson
(74) *Attorney, Agent, or Firm* — Knobbe, Martens, Olson & Bear, LLP

(57) ABSTRACT

Methods are described for augmenting cerebral blood flow and altering sympathetic nerve firing and catecholamine release by cooling a part of the body. In particular localized cooling of the nose or mouth is used to augment cerebral blood flow and alter sympathetic nerve firing. By cooling a localized area such as nose or mouth, release of norepinephrine after an ischemic event is inhibited. The methods described may be applied to augment cerebral blood flow and alter catecholamine release, particularly in treatment of stroke, heart attack and transient ischemic event.

20 Claims, 9 Drawing Sheets

Baseline, T=38.0

PC 5, T=37.5

PR 10, T=36.6

PR 30, T=32.5

COOLING OF LOCALIZED AREAS OF THE BODY FOR CEREBRAL BLOOD FLOW AUGMENTATION

RELATED APPLICATIONS

This application claims priority to U.S. Provisional Application No. 61/104,619, filed Oct. 10, 2008, which is incorporated herein by reference.

BACKGROUND OF THE INVENTION

1. Field of the Invention

Embodiments of the invention relate to methods of altering sympathetic nerve firing and augmenting cerebral blood flow. Methods are described for treatment of individuals in need of augmented cerebral blood flow, such as during and after stroke, transient ischemic attack and myocardial infarction.

2. Description of the Related Art

Therapeutic hypothermia is the use of hypothermia to cool the brain to provide neuroprotection. Therapeutic hypothermias have potential for treating ischemic insult when the brain is deprived of oxygen by cardiac arrest, stroke or brain trauma.

Animal studies have shown therapeutic hypothermia to be an effective neuroprotectant (Krieger, Derk. et al. "Cooling for Acute Ischemic Brain Damage." American Heart Association. May 25, 2001, pg. 1847-1854) and that cooling the ischemic brain can provide neuroprotection (Polderman, Kees H. "Application of therapeutic hypothermia in the ICU." Intensive Care Med. (2004) 30:556-575).

Therapeutic hypothermia has been endorsed by the American Heart Association (AHA) and International Liason Committee on Resuscitation (ILCOR) for use after cardiac arrest. In one study, patients resuscitated 5-15 min. after collapse were cooled over a 24 hour period at a target temperature of 32-34° C. The group receiving the therapeutic hypothermia had a death rate that was 14% lower than the group receiving standard care (Holzer, Michael "Mild Hypothermia to Improve the Neurologic Outcome After Cardiac Arrest." New England Journal of Medicine. (2002) Vol. 346, No. 8).

While it is known that mild hypothermia (32-34° C. (89.6-93.2° F.)) is effective in treatment of ischemia, there are problems with lowering body temperature to 32-34° C. One problem is that normally at around 36° C. (96.8° F.) the patient will begin to shiver and drugs such as Desflurane and Demerol must be administered to inhibit the shiver response. Other side effects include arrhythmia, decreased clotting threshold, increased risk of infection, and electrolyte imbalance. Furthermore, the physician must take care to rewarm the patient gradually to avoid spikes in intracranial pressure.

Furthermore, body cooling is generally accomplished by either an invasive method such as a catheter or a non-invasive method such as a water blanket. There are problems with these techniques.

Cooling catheters are placed in an appropriate vein or artery. A catheter placed into the femoral vein near the heart can cool the entire body by circulating a saline solution through the catheter that is controlled by an exterior control unit. However, the technique is invasive and potentially may induce bleeding, vascular puncture, infection and deep vein thrombosis.

A non-invasive technique for lowering of body temperature is a water blanket. Water blankets may be applied by non-physician hospital personnel and do not require any insertion into the patient body. The drawbacks include danger of electric shock, freezer burns to the patient and difficulty in precisely controlling temperature.

While cold anywhere in the body can be neuroprotective, part of the neuroprotection may be due to enhanced cerebral blood flow (cbf). According to dogma, hypothermia leads to a progressive diminution of cbf, such that 1 degree reduction of body temperature results in a 10% reduction in cbf. However, several pieces of evidence suggest that the cerebrovascular response to cold may be biphasic and possibly even dependent on the mode of cooling.

U.S. Pat. No. 6,942,686 discloses regulation of cerebral blood flow by cooling or heating of an artery of the patient. U.S. Pat. No. 6,942,686 teaches relatively large temperature changes (cooling to 30° C. or below) in order to enhance cerebral blood flow.

It has been found by the inventors that very small decreases in body temperature (up to 1.5° C.) produce unexpectedly large increases in cbf. Furthermore, the increase in cbf was achieved without the necessity of lowering basal body temperature. Augmentation of cbf was achieved by selectively cooling only a part of the body such as the nose and/or mouth. Methods of enhancing cbf are disclosed with implications for treatment of ischemia.

SUMMARY OF THE INVENTION

Embodiments of the invention are directed to methods of augmenting cerebral blood flow, altering sympathetic nerve firing, and/or decreasing catecholamine levels by cooling a part of the body of a patient in need thereof.

Further embodiments are directed to methods of increasing cerebral blood flow during or after an ischemic event by cooling the nose and/or mouth of a patient in need thereof, whereby cerebral blood flow is increased.

Further aspects, features and advantages of this invention will become apparent from the detailed description of the preferred embodiments which follow.

BRIEF DESCRIPTION OF THE DRAWINGS

FIG. 2A: baseline, temperature=38.0° C., internal diameter of artery=0.33 cm, flow=427 ml/min; FIG. 2B: 5 minutes post-resuscitation, temperature=37.0° C., internal diameter of artery=0.48 cm, flow=560 ml/min; FIG. 2C: 10 minutes post-resuscitation, temperature=36.6° C., internal diameter of artery=0.50 cm, flow=518 ml/min; FIG. 2D: 30 minutes post-resuscitation, temperature=33.0° C., internal diameter of artery=0.48 cm, flow=150 ml/min.

DETAILED DESCRIPTION OF THE PREFERRED EMBODIMENT

Figure 1:
FIG. 1 shows cortical microvasculature assessed using optical coherence tomography (OCT) at baseline showing few vessels (Top left, Baseline, temperature=38.0° C.). Top right (post-cardiac 5 minutes, temperature=37.5° C.), following restoration of circulation, with a 0.5 degree temperature reduction, vessel caliber and capillary density is increased. Further increase is seen bottom left (post-resuscitation 10 minutes; temperature=36.6° C.), at 1 degree temperature reduction. At bottom right (post-resuscitation, 30 minutes, temperature=32.5° C.), at 4 degree temperature reduction, the vessel density is reduced compared to baseline.
Figure 1:
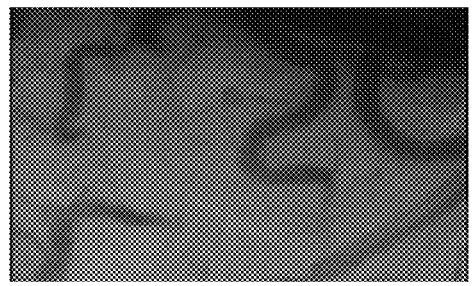
Figure 1:
Figure 1:
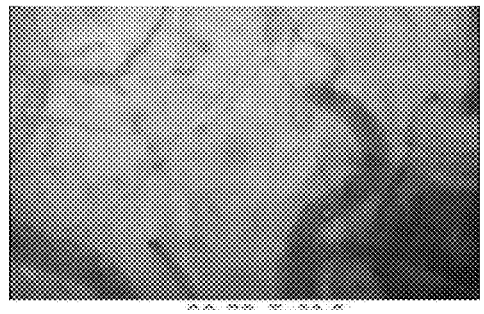
Figure 2A:
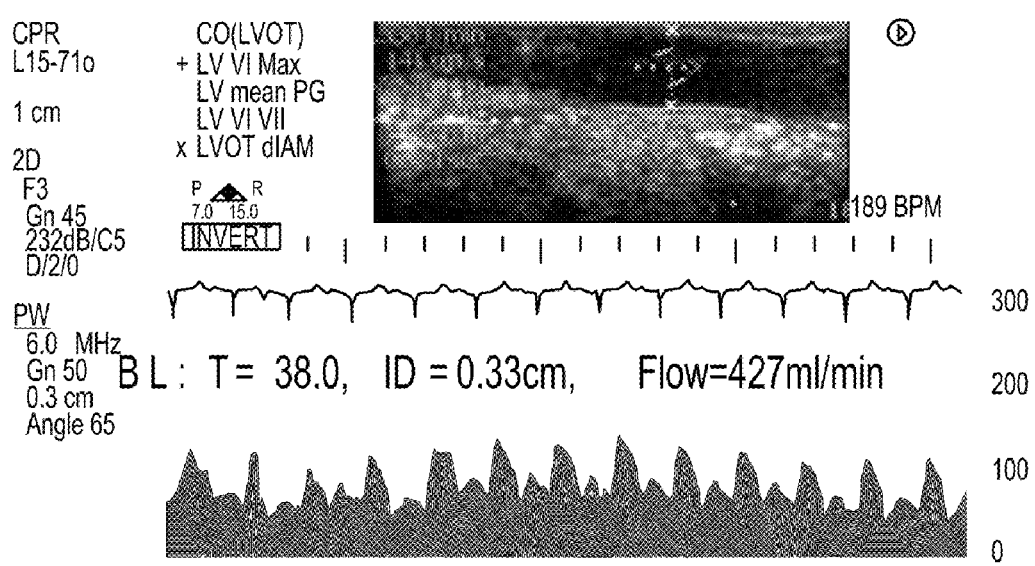
FIGS. 2A-2D shows that carotid artery diameter and carotid blood flow measured using ultrasonography increase steadily from baseline to 30 minutes post restoration of flow, corresponding to the increased capillary caliber and density seen in the cortex using OCT. Once a critical temperature reduction is surpassed, the reverse occurs, carotid flow falling well below baseline value.
Figure 2B:
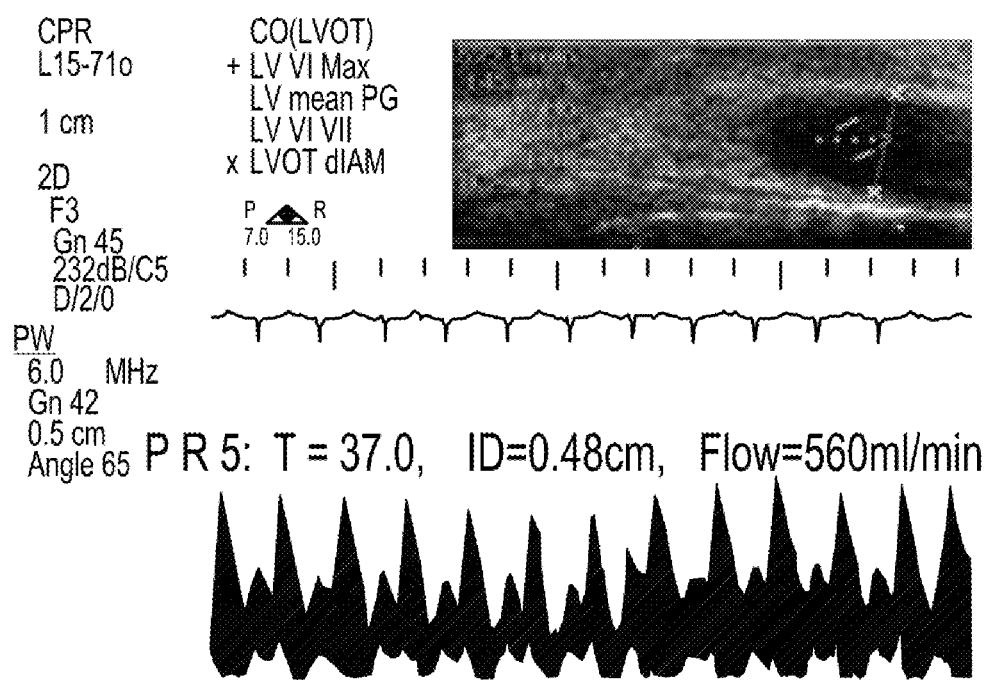
Figure 2C:
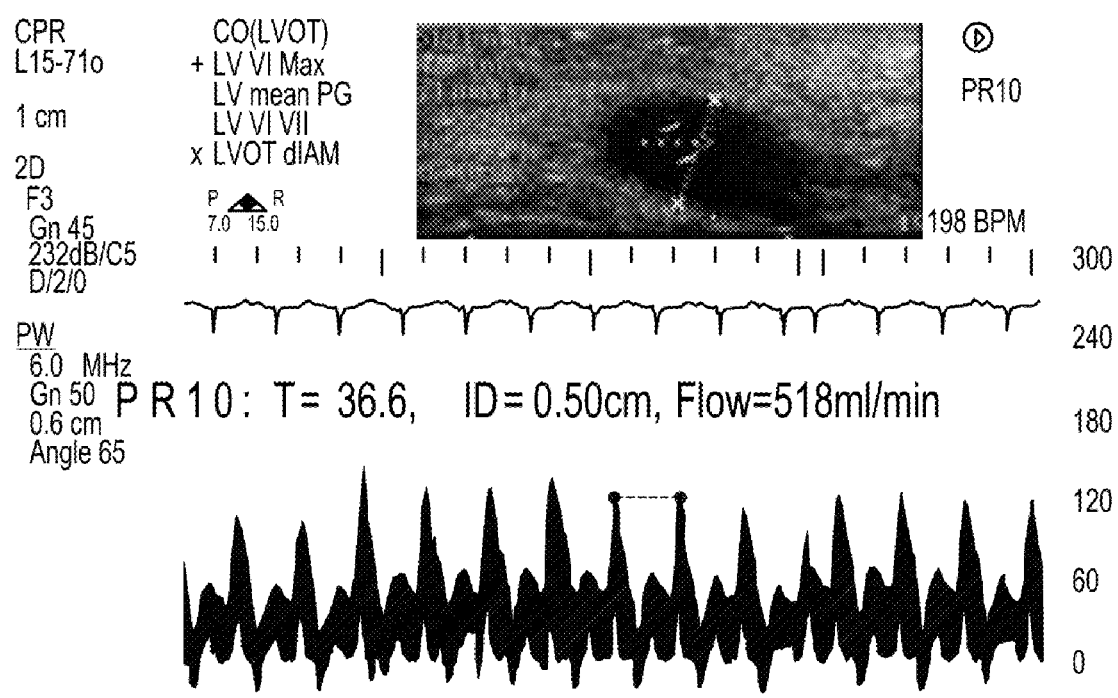
Figure 2D:
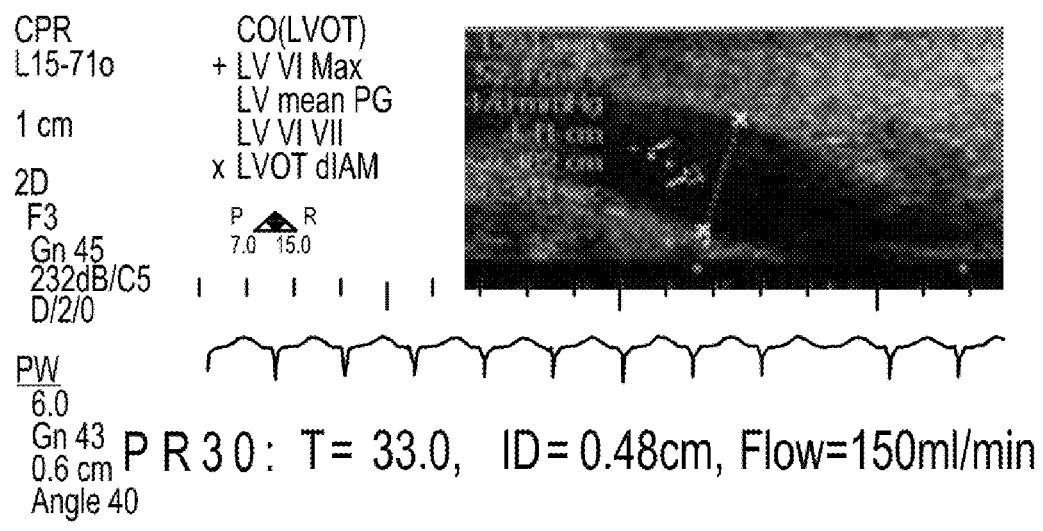

While the described embodiment represents the preferred embodiment of the present invention, it is to be understood that modifications will occur to those skilled in the art without departing from the spirit of the invention. The scope of the invention is therefore to be determined solely by the appended claims.

External cooling, as might occur during exposure to cold air, causes a peripheral vasoconstriction, but an increase in cardiac output and dilatation of the carotid arteries. The changes in systemic temperature, if any, accompanying this phenomenon have never been documented. Cross-sectional slices of carotid arteries in a Petri dish have also been shown to dilate upon cooling of the bathing fluid.

It has been found unexpectedly that cooling of a part of the body such as the nose and/or mouth increases cerebral blood flow (cbf) and may produce a beneficial treatment for ischemic insult without the risks associated with therapeutic hypothermia described above.

We have shown that minimal reduction of brain temperature (up to 1.5 degrees) induced by nasopharyngeal cooling, increases not just carotid flow but cerebral blood flow, whereas more dramatic reductions (5.5 degrees) decrease cerebral blood flow. This is attributable to the nasopharyngeal cooling because in uncooled control animals the opposite physiological response is observed. In the control animals, carotid diameter and cbf progressively diminish following restoration of circulation.

Embodiments of the invention are directed to where, a part of the body is cooled to a temperature of 0.5 to 4° C., preferably from 1-3° C., most preferably about 2° C. In some embodiments, the part of the body to be cooled is selected from mouth, nose, ear, pharyngeal area, head, neck, shoulders, arm, hand, finger(s), feet, toe(s), leg, body core or selected areas of any of the above. In some embodiments, more than one selected body part may be cooled simultaneously or sequentially. Preferably, the body part to be cooled is selected from the nose, mouth, pharynx, or a combination thereof.

In a preferred embodiment, the nasopharyngeal cavity is cooled using a commercially available device for this purpose. Typically, such devices spray a volatile liquid coolant into the nasal cavity to achieve a desired temperature. One such device is the RhinoChill System® (BeneChill, San Diego, Calif.). The RhinoChill System is a battery-operated non-invasive, portable, and easy-to-use medical device for rapid therapeutic patient cooling through the nasal cavity. The advantages of using the nasal cavity are that it is a natural orifice into the body, that it is in close proximity to the brain and that the nasal cavity is a natural heat exchanger.

The cooling may be initiated before, during or after an ischemic event and maintained for as long as determined to be beneficial to the patient. The treatment may be either continuous or discontinuous. Typically, the time of cooling is from 1 hour to 24 hours. In preferred embodiments the treatment is maintained sufficient to obtain the desired effect of augmented cbf. That is, cooling the mouth, nose and/or nasopharyngeal cavity to 0.5 to 4° C., preferably from 1-3° C., most preferably about 2° C. may be performed for 1-120 minutes, preferably 1-60 minutes, more preferably 1-30 minutes, yet more preferably 1-20 minutes, yet more preferably 1-10 minutes, yet more preferably 1-5 minutes and yet more preferably 1-2 minutes to achieve augmented cbf. When the cbf decreases, the treatment may again be applied.

It is an advantage of the present invention that the benefits observed with respect to increased cbf and dilation of arteries are obtained within minutes of applying the cold treatment to the nose, mouth and/or pharyngeal area. Within 1-2 minutes, carotid artery diameter increases and blood flow increases. As flow in brain cortex increases, collateral vessels increase also in density and number. Sympathetic nerves that end on carotid artery fire less often resulting in inhibition of the sympathetic nervous system.

In some embodiments, the effects on cbf are observed without depression of either the brain temperature or the body temperature. It is not essential that the brain temperature or body temperature be lowered during the cooling treatment. In some embodiments, there is no change in brain or body temperature as a result of cooling the selected body part. In some embodiments, the temperature of 0.5 to 4° C., preferably from 1-3° C., most preferably about 2° C. is maintained in the nose, mouth, or nasopharyngeal area for a longer period such as 30 minutes or more. In some embodiments, the brain temperature and body temperature eventually will drop. The standard of care for therapeutic hypothermia is to keep the patient at a body temperature of 33-34° C. for 12-24 hours. In embodiments of the invention, cooling of the nose, mouth and/or nasopharyngeal area is monitored such that body temperature remains above 33° C. and the body is not continuously cooled for more than 24 hours.

The body may be cooled in other areas to enhance cerebral blood flow. The effect of relatively short treatment of cooling to 0.5 to 4° C., preferably from 1-3° C., most preferably about 2° C. for 1-120 minutes, preferably 1-60 minutes, more preferably 1-30 minutes, yet more preferably 1-20 minutes, yet more preferably 1-10 minutes, yet more preferably 1-5 minutes and yet more preferably 1-2 minutes is to alter the sympathetic nerve firing rate to increase or decrease blood flow. In a preferred embodiment, the nose or mouth is cooled, thereby inhibiting the sympathetic system and increasing cbf.

By inhibiting the sympathetic nervous system, secretion of norepinephrine is also inhibited. The level of norepinephrine is indicative of sympathetic activity. If sympathetic activity is depressed or inhibited, then constriction of blood vessels will be inhibited.

An immediate effect of cardiac arrest is the "catecholamine storm" which is the body's reaction when the heart stops beating, increasing sympathetic activity, increasing constriction of blood vessels in an attempt to raise blood pressure. However, the "catecholamine storm" has very negative effects on final outcome for the patient which include brain death. Cooling of the nose, mouth and/or nasopharyngeal area reduces the catecholamine storm and reduces these deleterious effects.

In preferred embodiments, cooling of a body part alters sympathetic activity, blood flow and catecholamine levels. Preferably, the body part is selected from mouth, nose, ear, pharyngeal area, head, neck, shoulders, arm, hand, finger(s), feet, toe(s), leg, body core or selected areas of any of the above. In some embodiments, more than one selected body part may be cooled simultaneously or sequentially. Preferably, the body part to be cooled is selected from the nose, mouth, pharynx, or a combination thereof.

In preferred embodiments, mouth, nose, pharynx or combinations thereof are cooled, and sympathetic activity and catecholamine levels are inhibited. Catecholamine include norepinephrine and epinephrine. Preferably, catecholamine levels are inhibited by at least 10%, preferably at least 20%, more preferably at least 30%, more preferably at least 40%, more preferably at least 50%, more preferably at least 60%, more preferably at least 70% and more preferably at least 80% compared to the level expected for an individual under the same conditions but without treatment to cool selected body part(s).

Enhanced cerebral blood flow improves the chances of resuscitation after heart attack, protects heart function after ischemic insult, protects the brain after ischemic insult and has utility in treatment of any condition in which cbf is inadequate including but not limited to stroke, head injury, cardiac arrest, transient ischemic attack, Alzheimer's, and dementia.

Embodiments of the invention directed to administration of cooling to a body part such as nose or mouth, provide a big advantage for the patient. For example, the treatment may be administered immediately, by non-trained individuals. The physiological response is obtained very quickly, as soon as the body part is cooled. As it is not necessary to cool the entire body, it is not necessary to use a water blanket or cooling catheter, thus avoiding the disadvantages of these techniques such as the potential for electric shock and freezer burns (water blankets) and avoidance of bleeding, infection, vascular puncture, and deep vein thrombosis (cooling catheters).

EXAMPLES

Example 1

Effect of Cooling on Cerebral Blood Flow

Experiments were done with anesthetized live pigs. The brain was exposed so that blood vessels and blood flow could be viewed using an IR probe. Ventricular fibrillation (VF) was electrically induced to stop the heart. After 10 minutes, chest compression and defibrillation were initiated to resuscitate. The nose was cooled at a temperature of 2° C.; cooling was initiated 5 minutes prior to attempted defibrillation. Chest compression and defibrillation were continued for 15 minutes or until return of spontaneous circulation (ROSC). The nose was maintained at a temperature of 2° C. for 1 hour after initiation of CPR.

FIG. 1 shows cortical microvasculature assessed using optical coherence tomography (OCT) at baseline showing few vessels (upper left panel). The upper right panel shows blood vessels 5 minutes after initiation of chest compression (post compression, PC) and cooling of the nose. Following restoration of circulation, with a 0.5 degree temperature reduction, vessel caliber and capillary density is increased. The lower panels show 10 and 30 minutes post resuscitation (PR), respectively. Further increase is seen bottom left, at 1 degree temperature reduction. At bottom right, at 4 degree temperature reduction, the vessel density is reduced compared to baseline.

FIGS. 2A-D shows ultrasound images of the carotid artery in the neck. At baseline (FIG. 2A), vessel internal diameter is 0.33 cm and the flow is 427 ml/min. At 5 minutes post resuscitation (FIG. 2B), the body temperature has dropped by 1° C. Both the internal diameter of the vessel and blood flow have increased (0.48 cm and 560 ml/min respectively). At 10 minutes post resuscitation (FIG. 2C) internal diameter of vessel continues to increase and blood flow remains high at 0.50 cm and 518 ml/min, respectively. Body temperature has now lowered by 1.4° compared to baseline. However, at 30 minutes post resuscitation, upon further cooling to 33° C. (FIG. 2D), the vessel diameter now begins to decrease as does blood flow (0.48 cm and 150, respectively).

Figure 3:
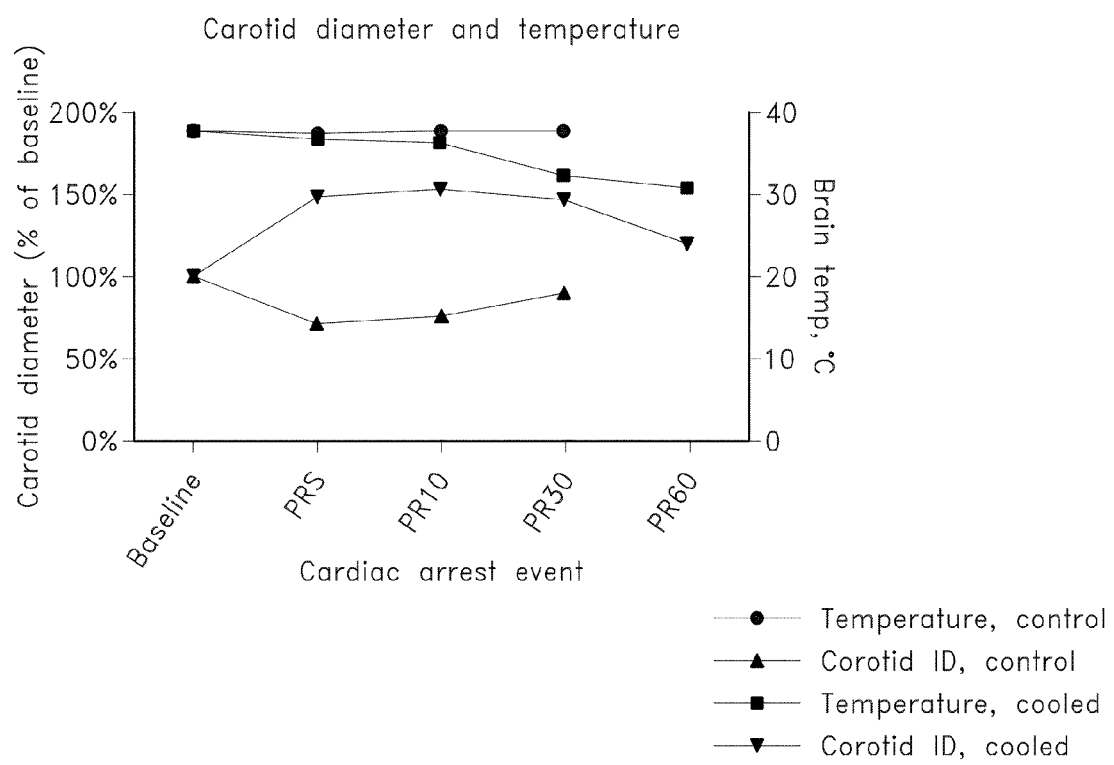
FIG. 3 shows changes in carotid diameter (as % of baseline) and temperature as a result of cooling the nose to 2° C. Measurements were taken before cardiac arrest (baseline), and at 5, 10, 30 and 60 minutes post-resuscitation. (top dashed line)=temperature, control group; (bottom solid line)=carotid artery internal diameter, control group; (bottom dashed line) =temperature, cooled group; (top solid line)=carotid artery internal diameter, cooled group.
Figure 4:
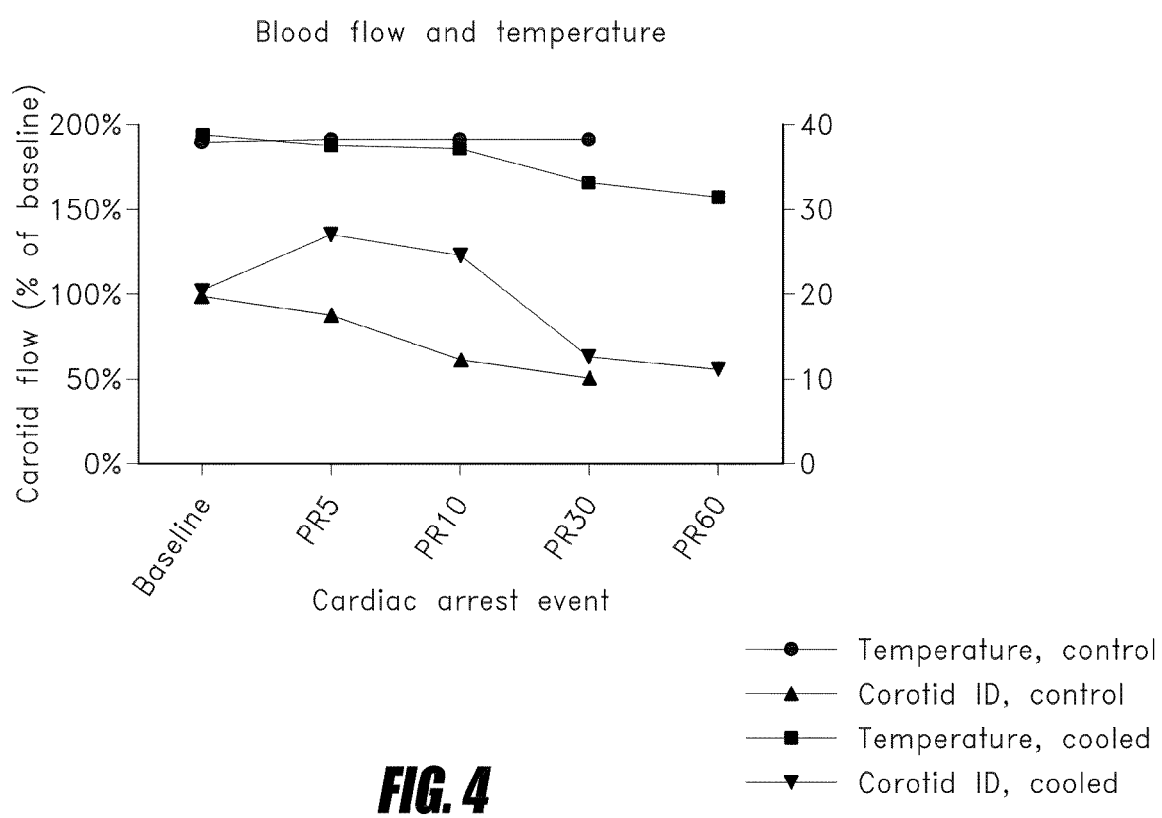
FIG. 4 shows changes in blood flow (as % of baseline) and temperature as a result of cooling the nose to 2° C. Measurements were taken before cardiac arrest (baseline), and at 5, 10, 30 and 60 minutes post-resuscitation. (upper dashed line) =temperature, control group; (bottom solid line)=carotid artery internal diameter, control group; (bottom dashed line) =temperature, cooled group; (upper solid line)=carotid artery internal diameter, cooled group.

The data of FIGS. 2A-2D is shown graphically in FIGS. 3 and 4. FIG. 3 plots carotid diameter and brain temperature at different time points before cardiac arrest (baseline) and post-resuscitation (PR).

FIG. 4 shows blood flow over the same time course and plots blood flow and brain temperature before cardiac arrest (baseline) and post-resuscitation (PR).

As can be seen from FIGS. 3 and 4, increases in carotid diameter (FIG. 3) and blood flow (FIG. 4) are greatest within the first 10 minutes post-resuscitation. during the time period, brain temperature drops only slightly, 1.5° C. or less. As cooling of the mouth continues and brain temperature continues to drop, carotid diameter and blood flow decrease and approach levels of uncooled control.

The data has several important implications. First, positive physiological effects are observed after cooling only the nose to 2° C. for a short period of time (5-10 minutes PR). Important physiological effects are increased diameter of carotid artery and augmented cerebral blood flow. Moreover, these effects are accompanied by very slight changes in overall brain temperature (up to 1-1.4° C.). Further decreases in brain temperature (to 5.5° C.) reversed the effect. Cerebral blood flow decreased. We conclude that very small changes in brain temperature can produce dramatic increase in cerebral blood flow. Indeed, changes in brain and/or body temperature may not be necessary at all. By cooling only the nose, increased artery diameter and cerebral blood flow are observed.

Example 2

Effect of Cooling on Sympathetic Nerve Firing

Figure 5:
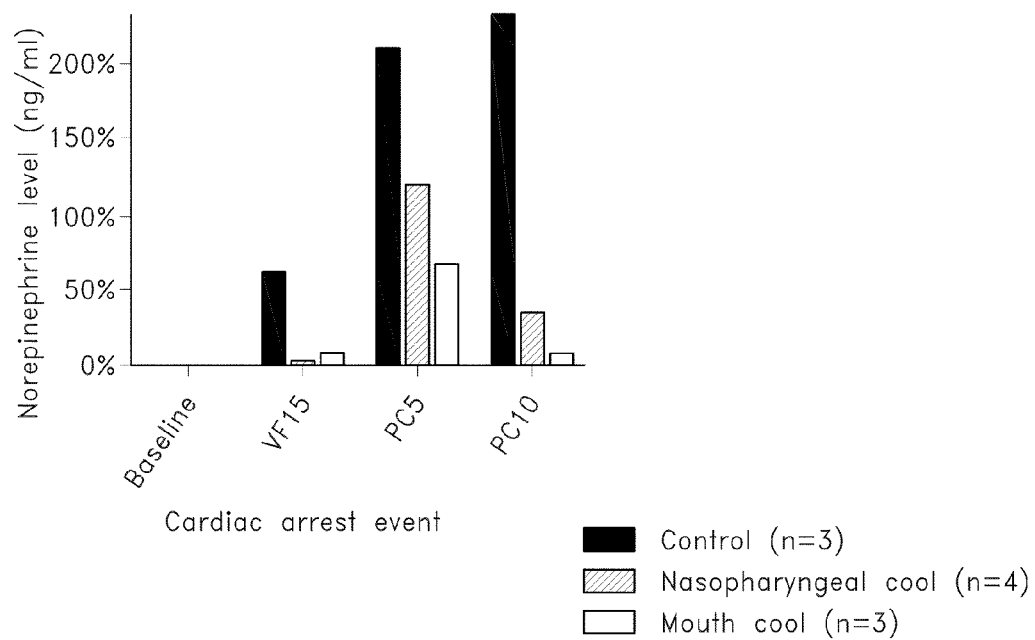
FIG. 5 shows catecholamine levels (norepinephrine, ng/ml) during cardiac arrest and reduction of catecholamine levels with nasal and oral cooling. Measurements were taken at baseline (before cardiac arrest), 15 minutes after ventricular fibrillation (VF) and at 5 and 10 minutes post-cardiac arrest.

The mechanism by which changes in nasopharyngeal temperature induce changes in cerebral blood flow may be secondary to sympathetic inhibition. We have documented reduction in the catecholamine surge which accompanies cardiac arrest. (FIG. 5).

Experiments were performed as described above for Example 1 except that in some cases the nose was cooled and in some cases the mouth was cooled. The control subjects did not receive a cooling treatment. As an indication of sympathetic nerve firing, levels of the catecholamine, norepinephrine, were measured (FIG. 5).

At VF15, before commencement of resuscitation, the controls have low levels of norepinephrine and the cooled subjects have virtually no norepinephrine. At 5 and 10 minutes post cardiac arrest, the levels of norepinephrine in the controls spikes up above 200 ng/ml, while the levels in the cooled subjects (both mouth cooling and nasopharyngeal cooling) remain much lower.

Cooling of either the mouth or nasopharyngeal area inhibits that catecholamine surge that is observed during cardiac arrest.

Figure 6:
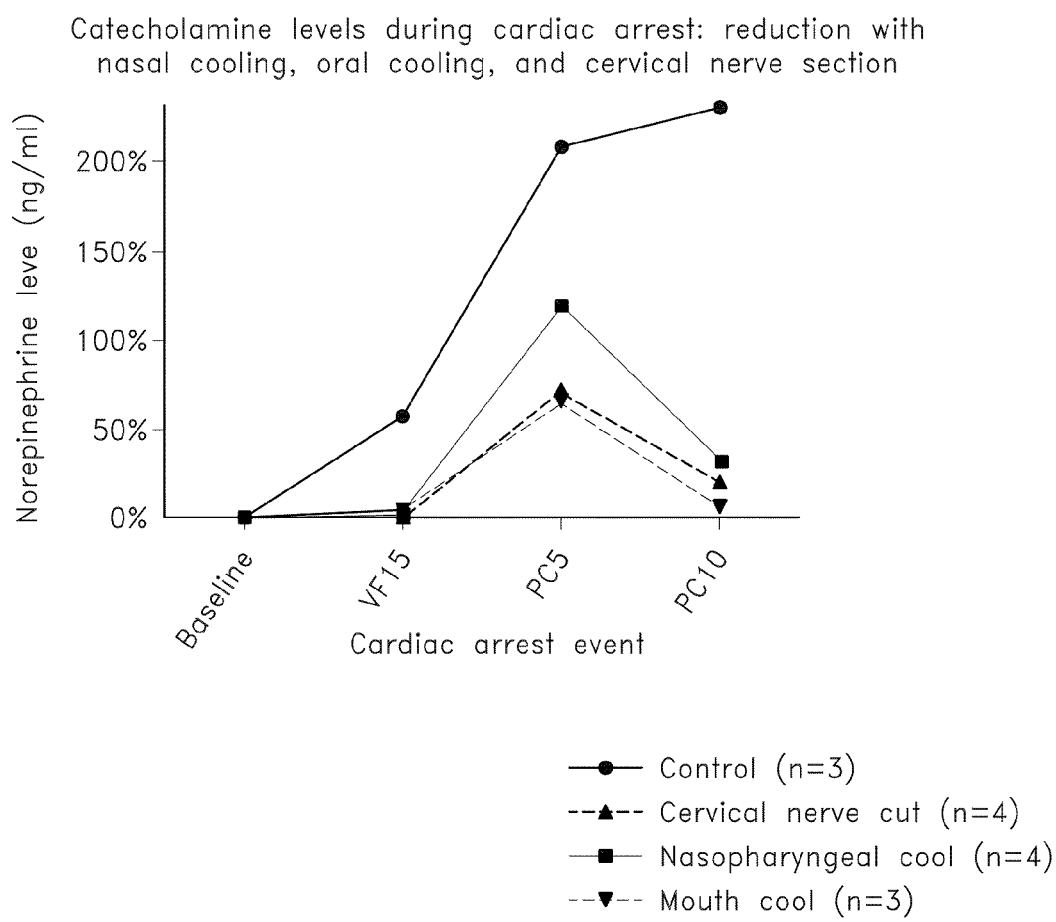
FIG. 6 shows catecholamine levels during cardiac arrest: reduction with nasal cooling, oral cooling and cervical nerve section. Measurements were taken at baseline (before cardiac arrest), 15 minutes after ventricular fibrillation (VF) and at 5 and 10 minutes post-cardiac arrest. Control top line (●) (n=3); Cervical nerve cut (▲) (n=4); Nasopharyngeal (nose) cooling (■) (n=4); and mouth cooling (▼) (n=3).

FIG. 6 shows data in comparison with cutting of the cervical sympathetic nerve. Severing of the cervical sympathetic nerve cuts off norepinephrine release. Experiments were performed as described above. It can be seen from FIG. 6 that by cooling either the mouth or nasopharyngeal area, release of norepinephrine is even less than observed by cutting of the cervical nerve. Cooling of the nose or mouth is a surprisingly effective inhibitor of norepinephrine release, more effective then cutting of the cervical sympathetic nerve.

It will be understood by those of skill in the art that numerous and various modifications can be made without departing from the spirit of the present invention. Therefore, it should be clearly understood that the forms of the present invention are illustrative only and are not intended to limit the scope of the present invention.

What is claimed is:

1. A method of augmenting cerebral blood flow comprising cooling a part of the body of a patient in need thereof, wherein cooling is discontinuous and is reapplied when the cerebral blood flow falls below a predetermined value.

2. The method of claim 1, wherein the part of the body is selected from nose, mouth, pharynx, hands, feet, finger(s), toe(s), neck, shoulders and combinations thereof.

3. The method of claim 1, wherein the body part is cooled to 0.5 to 4° C.

4. The method of claim 1, wherein the body part is cooled to 1-3° C.

5. The method of claim 1, wherein the body part is cooled to about 2° C.

6. The method of claim 1, wherein cooling is for 1-60 minutes.

7. The method of claim 1, wherein cooling is transcutaneous or endovascular.

8. The method of claim 1, wherein the method comprises cooling the nose or mouth.

9. The method of claim 8, wherein cooling is by a nasopharyngeal device.

10. The method of claim 1, wherein cerebral blood flow is measured by transcranial Doppler or Carotid Doppler.

11. The method of claim 1, wherein sympathetic firing is inhibited.

12. A method of increasing cerebral blood flow during or after an ischemic event comprising cooling the nose and/or mouth of a patient in need thereof, wherein cooling is discontinuous and is reapplied when the cerebral blood flow falls below a predetermined value, and whereby cerebral blood flow is increased.

13. The method of claim 12, wherein cooling the nose and/or mouth is to 0.5 to 4° C.

14. The method of claim 12, wherein cooling the nose and/or mouth is to 1-3° C.

15. The method of claim 12, wherein cooling the nose and/or mouth is to about 2° C.

16. The method of claim 12, wherein cooling is for 1-60 minutes.

17. The method of claim 12, wherein the method comprises cooling the nose.

18. The method of claim 17, wherein cooling is by a nasopharyngeal device.

19. The method of claim 12, wherein cerebral blood flow is measured by transcranial Doppler or Carotid Doppler.

20. The method of claim 12, wherein the ischemic event is selected from the group consisting of cardiac arrest, stroke, and transient ischemic attack.

* * * * *